United States Patent [19]

Grubbs, Jr. et al.

[11] Patent Number: 4,843,015

[45] Date of Patent: Jun. 27, 1989

[54] METHOD FOR DETERMINING VOLATILE PHOSPHORUS IN CARBON

[75] Inventors: John R. Grubbs, Jr., Mt. Pleasant; Aravamuthan P. Sarathy, James Island; Robert C. Flowe, Summerville, all of S.C.

[73] Assignee: Westvaco Corporation, New York, N.Y.

[21] Appl. No.: 116,973

[22] Filed: Nov. 5, 1987

[51] Int. Cl.$^4$ ...................... G01N 31/12; G01N 33/00
[52] U.S. Cl. ..................... 436/103; 422/80; 436/155; 436/164
[58] Field of Search ............... 436/103–105, 436/38, 155, 164, 167, 181, 177; 422/78, 80, 130

[56] References Cited

U.S. PATENT DOCUMENTS

| | | | |
|---|---|---|---|
| 3,425,805 | 2/1969 | Grobin | 436/103 |
| 3,796,543 | 3/1974 | Kamphake | 436/103 |
| 3,847,554 | 11/1974 | Su | 422/80 |
| 4,419,328 | 12/1983 | Walsh | 422/78 |
| 4,473,651 | 9/1984 | Goldstein | 436/60 |
| 4,533,639 | 8/1985 | Kojima et al. | 436/103 |
| 4,599,316 | 7/1986 | Hahn et al. | 436/105 |
| 4,627,910 | 12/1986 | Millman | 208/111 |

FOREIGN PATENT DOCUMENTS

| | | | |
|---|---|---|---|
| 7806645 | 12/1978 | Netherlands | 436/103 |
| 8004781 | 11/1980 | Netherlands | 436/103 |

Primary Examiner—Barry S. Richman
Assistant Examiner—Lyle Alfandary-Alexander
Attorney, Agent, or Firm—Terry B. McDaniel; Richard L. Schmalz

[57] ABSTRACT

A method and apparatus for determining the phosphorus content which can be volatilized in a solid carbon sample. The sample is heated in the presence of steam to produce a vaporous steam containing volatile phosphorus. Next, the vaporous stream is passed through a zinc oxide layer whereby the voliatle phosphorus is retained. A colored solution is formed upon adding to the zinc oxide layer a vanadate-molybdate reagent. Finnally, the intensity of the colored solution is determined by a spectrophotometer; and the phosphorus content is determined by comparison with a standard intensity graph.

19 Claims, 2 Drawing Sheets

CONFIGURATION OF CARBON SAMPLE IN REACTOR

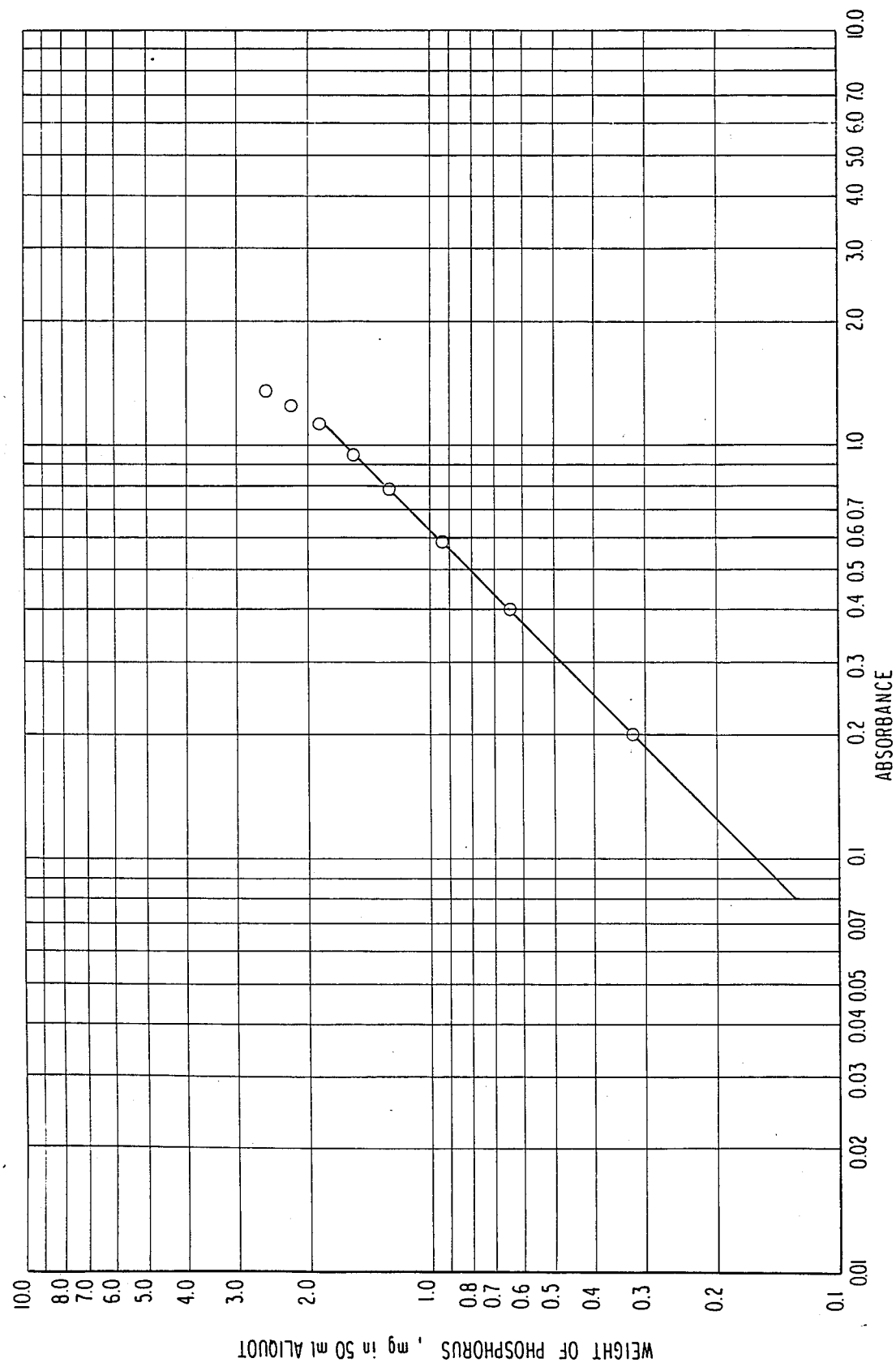

METHOD FOR DETERMINING VOLATILE PHOSPHORUS IN CARBON

BACKGROUND OF THE INVENTION

The sweetener industry employs wood-based carbon as an adsorber and filter medium for processes such as deashing and decolorization. When wood-based carbon is regenerated in the presence of steam, volatile phosphorus is released. This phosphorus, in elemental form or in the form of phosphates, is known to cause severe deterioration of the insulation in regeneration furnaces, the tubes of waste heat boilers, and parts of other regeneration equipment.

It would therefore be beneficial to have an analytical procedure to monitor volatile phosphorus released from wood-based carbon at regeneration conditions and such method should not require total phosphorus analysis. The desired method for determining the amount of volatile phosphorus in a carbon sample should be easy to perform and highly accurate.

Various methods for determining phosphorus content are known in the prior art. U.S. Pat. No. 4,599,316 to Hahn et al discloses a spectrophotometric method for determining the concentration of inorganic phosphate in a sample fluid, such as bodily fluids. An ammonium molybdate reagent is employed as a complexing agent.

In U.S. Pat. No. 3,796,543 to Kamphake, a continuous automatic system is employed for measuring the amount of phosphates in aqueous fluids, e.g., sewage effluent. This analytical technique is based on what is known as the molybdenum blue reaction.

U.S. Pat. No. 4,533,639 to Kojima et al discloses a colorimetric analytical method for determining the amount of phosphate in a phosphate-containing coating stripped from a ferrous metal surface.

U.S. Patent No. 3,425,805 to Grobin, Jr. discloses a colorimetric method for determining the phosphite content of electroless plating baths. A molybdate ion complex is formed in solution with the phosphite ions.

None of the above-mentioned analytical methods, however, are directed to problems associated with carbon used as a sorbent generally, and in particular, determining the volatile phosphorus content of solids such as carbon. Thus, there is still a present need for an accurate and efficient analytical technique for such phosphorus determinations.

OBJECTS AND SUMMARY OF THE INVENTION

An object of the present invention is to provide a simple and accurate analytical technique for determining the volatile phosphorus content of various substances.

Another object of the present invention is to provide an analytical technique for measuring volatile phosphorus released from wood-based carbons at regeneration conditions.

Still another object of the present invention is a method for analyzing phosphorus compounds in an off-gas stream from a plant operation.

Briefly stated, volatile phosphorus contained on wood-based carbon is first removed by reaction with steam at elevated temperatures. Nitrogen or helium by themselves do not strip phosphorus from the carbon at the elevated regeneration temperature. The phosphorus released in the off-gas is then captured by a layer of granulated zinc oxide as zinc phosphate. It appears that all forms of phosphorus compounds (hypo-, pyro-, and polyphosphates) are converted to the orthophosphate form by zinc oxide and retained as zinc orthophosphate. The orthophosphate radical of zinc orthophosphate is then determined by a spectrophotometric method based on vanado-molybdo reagent. The optical intensity of the resulting yellow color is directly proportional to the phosphate concentration in the solution.

According to the present invention, there is provided a combustion reactor comprising an open-ended elongated quartz tube having arranged therein a plurality of beds (or layers) which are separated by quartz wool or the like. Preferably, individual layers formed of the phosphorus-containing carbon sample, granulated quartz, and zinc oxide are provided. The combustion reactor is heated and operatively connected to a source of steam at one end and to a water collection system comprising a condenser and a collector at the other end. The combustion reactor is heated while steam is passed through the beds for a time sufficient to strip the phosphorus from the carbon sample. If desired, an inert gas such as nitrogen is passed through the combustion reactor prior to the passage of steam to purge air from the system.

The combustion reactor is removed from the heating apparatus and the reacted zinc oxide is collected and contacted with a standard solution comprising molybdate and vanadate ions to obtain a colored soluble phosphate complex solution. By measuring the intensity of the colored solution and comparing the measured color intensity to a known standard, the volatile phosphorus content in the solid carbon sample is determined.

Thus, the orthophosphate radical of zinc orthophosphate can be quantitatively analyzed by a spectrophotometric method after formation of a colored solution by reaction with a vanadate-molybdate reagent. The optical intensity of the yellow color is directly proportional to the phosphate concentration in the solution.

DESCRIPTION OF THE DRAWINGS

FIG. 2 is a calibration curve used for phosphorus determinations according to the present invention.

DETAILED DESCRIPTION OF THE INVENTION

Figure 1:
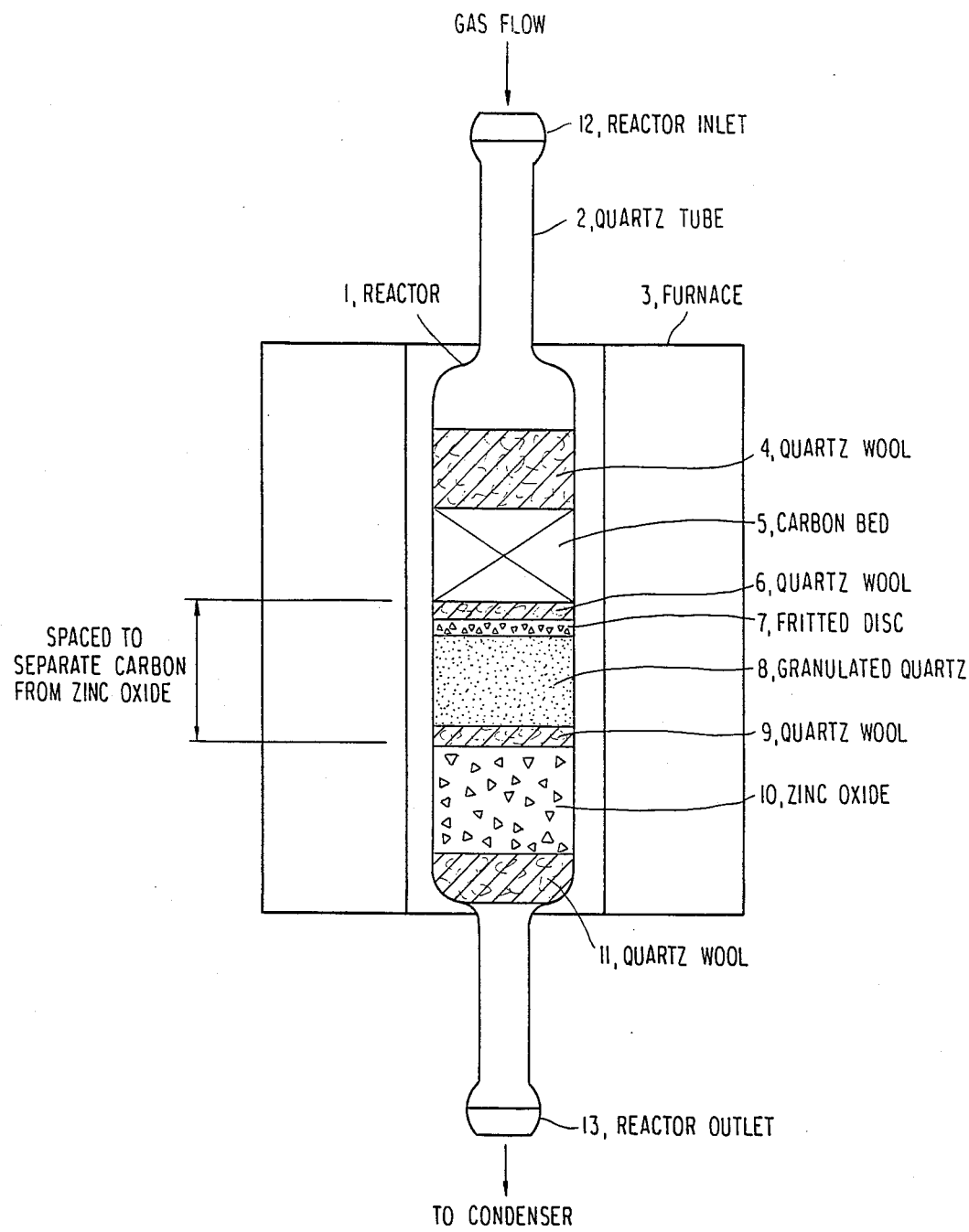
FIG. 1 is a schematic representation of a combustion reactor tube employed in the method of the present invention.

Referring to FIG. 1, a combustion reactor 1 for performing the analytical method of the present invention is shown. Reactor 1 comprises a quartz tube housing 2 packed with, from top to bottom, a quartz wool layer 4, a carbon bed 5 weighing from about 2 g to about 10 g, a quartz wool layer 6, a fritted disc 7, a granulated quartz layer 8 measuring from about 0.5 in. to about 2 in. thick, a quartz wool layer 9, a zinc oxide layer 10 weighing from about 10 g to about 40 g, and a quartz wool layer 11. Inert gas, such as, nitrogen, and steam pass through the reactor 1 via inlet 12 and outlet 13.

A heating furnace 3 surrounds the reactor 1 and maintains the temperature of the beds at about 1600° F. or above. Thus, the carbon particles in bed 5 are heated to a temperature of about 1600° F. while steam is passed through the carbon for at least one hour.

In the reactor 1, the zinc oxide layer is preferably granulated or powdered zinc oxide. When the phosphorus-containing steam contacts the zinc oxide particles in bed 10, zinc phosphate, or more specifically zinc orthophosphate, is formed and retained therein until a spectrophotometric analysis is made, as will be explained in greater detail hereinafter.

It is known that wood-based carbon sorbents which are loaded with volatile phosphorus are conventionally regenerated with steam at elevated temperatures. Phosphorus which is stripped from carbon particles may contain all forms of phosphorus compounds, such as, pyrophosphates ($P_2O_7^{-4}$), hypophosphates ($P_2O_6^{-4}$), orthophosphates ($PO_4^{-3}$), and metaphosphates ($PO_3^{-}$). In the present invention, volatile phosphorus compounds carried by the steam are passed through a layer of granulated zinc oxide where they are retained. Although not wishing to be bound by any particular theory, it appears that the phosphorus compounds which contact zinc oxide are converted to the orthophosphate form and retained in the zinc oxide bed as zinc orthophosphate.

The following non-limiting examples are included to more fully set forth the present invention.

EXAMPLE 1

Preparation of Vanadate-Molybdate Reagent

An ammonium molybdate tetrahydrate, i.e., (($NH_4)_6Mo_7O_{24}.4H_2O$)), sample weighing 25 g was dissolved in 250 ml of distilled and deionized water to form Solution A. Then, 1.25 g of ammonium metavanadate were dissolved in 200 ml of distilled and deionized water to prepare a solution to which is added 330 ml of concentrated hydrochloric acid to form Solution B. Solution A and Solution B were mixed together and diluted to a 1 liter volume, thereby forming a standard vanadate-molybdate reagent solution.

EXAMPLE 2

Preparation of Spectrophotometer Calibration Curve

A calibration curve was prepared using a Spectronic 210 UV spectrophotometer (Bausch and Lomb) by adding the following volumes of standard phosphoric acid solution to 50 ml volumetric flasks: 0.0 (blank), 1.0, 2.0, 3.0, 4.0, 5.0, 6.0, 7.0 and 8.0 ml. The standard phosphoric acid solution is prepared by adding one gram of concentrated reagent grade phosphoric acid to one liter of distilled-deionized water. For proper color development the pH of the solution must be adjusted to a level between 2 and 10. Reagent grade ammonium hydroxide was used to bring the pH to the required range. After adjusting the pH to 7, the volume was increased to 40 ml with distilled-deionized water. Ten ml of vanadate-molybdate reagent was added to each flask. After 20 minutes, the absorbance of the blank, versus distilled-deionized water was read on the Spectronic 210 spectrophotometer at 400 nm in 10 mm cells. The absorbance of each of the eight concentrations prepared, versus the blank, was then measured. Absorbance (abscissa) versus milligrams phosphoric acid (ordinate) data were plotted on 2 by 3 cycle logarithmic paper to yield a calibration curve which is useful for the life of the vanadate-molybdate reagent. The calibration curve obtained by the foregoing procedure is shown in FIG. 2.

EXAMPLE 3

Experimental Method

The reactor 1, made of quartz, was prepared by initially placing a plug of quartz wool 6 onto the fritted disc 7. A layer 5 of granular or powdered carbon (5 g) was then added, followed by an additional quartz wool layer 4 to secure the carbon bed. The tube was inverted to load the remaining sections of the reactor. A 1" thick layer 8 of sized granular quartz was added to the tube 1 followed by another layer 9 of quartz wool to support the granular quartz layer 8. The zinc oxide layer 10 was formed by adding 20 g of 4×20 mesh granulated zinc oxide. A quartz wool layer 11 was placed over the zinc oxide layer.

Appropriate inlet and outlet fittings were added and connected, and the reactor tube was positioned inside the furnace 3. Nitrogen was initially passed through the reactor tube 1 to flush air out of the system. The reactor furnace 3 was turned on and the temperature raised to 1600° F. After the desired temperature was reached and stabilized for 10 minutes, steam from a steam generator (not shown) and nitrogen were introduced for one hour. The resulting condensate was collected. At the end of the run the reactor was cooled to ambient temperature. The carbon was removed from the tube and weighed. The steam recovery was calculated based on the following formula:

Steam Recovery, % =

$$\frac{\left[\begin{array}{c} H_2O \text{ recovered} \\ \text{as condensate} \end{array}\right] + 1.5 \left[\begin{array}{c} \text{carbon charge} - \\ \text{carbon recovered} \end{array}\right]}{\text{Water fed to steam generator}} \times 100$$

The zinc oxide particles, wet with condensate from this run, were removed, diluted in volume to 100 ml, and digested with concentrated hydrochloric acid in a 250 ml Erlenmeyer flask. The digested zinc oxide was cooled and saved. The remaining quartz wool and quartz granules were removed from the reactor and washed with HCl. The quartz tube was rinsed with HCl followed by distilled water. Filtered washings were added to the 250 ml Erlenmeyer flask and saved. The flask was brought to volume with distilled-deionized water. The saved solutions was analyzed for phosphorus using the procedure described below.

A 1 ml aliquot was taken from the sample solution to be analyzed and added to 30 ml of distilled-deionized water in a 50 ml volumetric flask. One drop of concentrated ammonium hydroxide was then added, followed by the addition of 10 ml of the standard vanadate-molybdate reagent. The solution volume in the flask was increased to 50 ml by the addition of distilled-deionized water. Color was allowed to develop for 10 minutes. A sample of the colored solution was placed in a 10 mm light path cell and the cell inserted in the Spectronic 210 spectrophotometer. The absorbance reading was taken and compared against the previously prepared calibration curve of FIG. 2 to determine the phosphorus content in the aliquot. The amount of phosphorus in the entire sample solution was then calculated. The percent of volatile phosphorus in the carbon sample was calculated as follows:

$$\% \text{ volatile phosphorus} = \frac{w(250)}{W(1000)} \times 100 = \frac{w}{W} (25)$$

where: W=initial weight of carbon sample (g); and w=weight of phosphorus (mg) (in 1 ml aliquot).

EXAMPLE 4

Results of Zinc Oxide Test Method

Test results show that the method of the present invention, described as the zinc oxide method, accurately accounts (within 1.5%) for all of the phosphorus volatilized during steam treatment at regeneration conditions. Carbon volatile phosphorus concentrations determined by the zinc oxide method were verified using data obtained from Element Analysis Corporation in Tallahassee, Fla. Samples of loaded and regenerated carbon from various trials were sent to Element Analysis Corp. for phosphorus analysis using the Proton Induced X-ray Emission (PIXE) technique. Typical results in Table 1 show that volatile phosphorus concentrations determined using the zinc oxide method were within 1.5% of results obtained using PIXE analysis.

For example, in Trial 1, the reactor was prepared as described above containing 4.85 g of dry carbon. Steam was passed through the reactor for one hour at a carbon bed temperature of 1600° F. Volatile phosphorus concentration in the carbon determined using the zinc oxide method was 62.0 mg compared to 61.1 mg determined by the PIXE method. Thus, volatile phosphorus measured by the zinc oxide method was within 1.5%, i.e., $((62.0-61.1)\div 61.1)\times 100$, of that measured by PIXE analysis.

TABLE 1

Zinc Oxide Method Provides Good Determination of Volatile Phosphorus in Carbon

| Trial No. | Carbon Charge (dry basis) (g) | Volatile Phosphorus Content by ZnO Method, (mg) | Volatile Phosphorus Content by PIXE* Analysis, (mg) | Difference Between ZnO Method and PIXE Results (%) |
|---|---|---|---|---|
| 1 | 4.85 | 62.0 | 61.1 | 1.5 |
| 2 | 4.75 | 62.0 | 61.1 | 1.5 |
| 3 | 4.51 | 67.0 | 66.3 | 1.1 |

*PIXE = Proton Induced X-ray Emission

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method for determining the volatile phosphorus content in a solid sorbent comprising the steps of:
   heating the solid sorbent and liberating the phosphorus contained therein in gaseous form;
   passing the liberated gases through a zinc oxide layer and retaining the volatile phosphorus therein;
   forming a colored solution comprising the zinc oxide layer and a vanadate-molybdate reagent;
   determining the intensity of the colored solution by means of a spectrophotometer; and
   determining the content of phosphorus by comparison with a standard intensity graph.

2. A method according to claim 1 wherein the zinc oxide layer comprises granulated or powdered zinc oxide.

3. A method according to claim 1 wherein the liberated phosphorus is retained in the zinc oxide layer by reacting with zinc oxide to form zinc orthophosphate.

4. A method according to claim 3 wherein the vanadate-molybdate reagent is prepared from ammonium vanadate and ammonium molybdate.

5. A method according to claim 1 wherein the solid sorbent is carbon which is heated to an elevated temperature.

6. A method according to claim 5 wherein the elevated temperature is at least about 1500° F.

7. A method according to claim 5 wherein steam is employed to liberate the volatile phosphorus from the carbon.

8. A method according to claim 5 wherein the carbon used is a wood-based carbon which is heated in the presence of steam.

9. A method according to claim 8 wherein said steam is passed through the carbon.

10. A method for determining the phosphorus content in a solid phosphorus-containing carbon sample which comprises the steps of:
    (a) preparing a combustion reactor comprising an open ended elongated tube having arranged therein a plurality of separated beds, the beds comprising, in an individual array, a weighed solid phosphorus-containing carbon sample, granulated quartz, and zinc oxide;
    (b) heating the combustion reactor;
    (c) concurrently with step (b) passing steam through the reactor for a period of time sufficient to regenerate the carbon sample;
    (d) cooling the combustion reactor and collecting the zinc oxide;
    (e) contacting the zinc oxide with a standard solution comprising molybdate and vanadate ions to obtain a colored solution;
    (f) measuring the intensity of the colored solution; and
    (g) comparing the measured color intensity to a standard to determine the phosphorus content in the solid carbon sample.

11. A method according to claim 10 wherein the solid carbon sample is obtained from a large mass of regenerable carbon in an amount of about 5 to 10 grams.

12. A method according to claim 10 wherein the combustion reactor is heated to a temperature above about 1575° F.

13. A method according to claim 10 wherein condensate water from the steam is collected and weighed to obtain amount of steam recovered.

14. A method according to claim 10 wherein an inert gas is passed through the combustion reactor prior to the passage of steam.

15. A method according to claim 14 wherein the inert gas is nitrogen.

16. Apparatus for determining the volatile phosphorus content of a solid comprising:
    means for heating a solid and liberating the phosphorus contained therein in gaseous form;
    means for passing the liberated gases through a zinc oxide layer;
    means for forming a colored solution comprising the zinc oxide layer and a vanadate-molybdate reagent;
    spectrophotometric means for determining the intensity of the colored solution by means of a spectrophotometer; and
    means for determining the content of phosphorus in the solution by comparison with a standard intensity graph.

17. The apparatus according to claim 16 comprising an elongated vessel containing therein said heating means and said liberated gases passing means wherein said passing means is spaced from said heating means so that zinc oxide layer is not in contact with a solid sample positioned within said heating means.

18. The apparatus according to claim 17 wherein the heating means comprises a jacket furnace which surrounds a vessel.

19. The apparatus according to claim 17 wherein a layer of granulated quartz is positioned between the heating means and zinc oxide layer.

* * * * *

UNITED STATES PATENT AND TRADEMARK OFFICE
CERTIFICATE OF CORRECTION

PATENT NO. : 4,843,015
DATED      : June 27, 1989
INVENTOR(S): John R. Grubbs, Jr. et al.

It is certified that error appears in the above-indentified patent and that said Letters Patent is hereby corrected as shown below:

ON THE TITLE PAGE:

In the abstract, line 4, delete "steam" and substitute therefor --stream--.

In the abstract, line 8, delete "Finnally" and substitute therefor --Finally--.

In Claim 8, column 6, line 13, delete "used".

Signed and Sealed this

Twenty-fifth Day of January, 1994

Attest:

BRUCE LEHMAN

*Attesting Officer*    *Commissioner of Patents and Trademarks*